(12) United States Patent
Kulick

(10) Patent No.: US 9,968,424 B1
(45) Date of Patent: May 15, 2018

(54) SYSTEM, METHOD AND APPARATUS FOR CEMENTLESS RETENTION OF DENTAL CROWNS TO IMPLANTS

(71) Applicant: Walter Kennedy Kulick, Coral Springs, FL (US)

(72) Inventor: Walter Kennedy Kulick, Coral Springs, FL (US)

(*) Notice: Subject to any disclaimer, the term of this patent is extended or adjusted under 35 U.S.C. 154(b) by 0 days. days.

(21) Appl. No.: 15/717,329

(22) Filed: Sep. 27, 2017

(51) Int. Cl.
*A61C 8/00* (2006.01)

(52) U.S. Cl.
CPC .......... *A61C 8/0068* (2013.01); *A61C 8/0022* (2013.01); *A61C 8/0054* (2013.01); *A61C 8/0056* (2013.01)

(58) Field of Classification Search
CPC .... A61C 8/0068; A61C 8/0054; A61C 8/0056
See application file for complete search history.

(56) References Cited

U.S. PATENT DOCUMENTS

| | | | | |
|---|---|---|---|---|
| 5,073,111 A * | 12/1991 | Daftary | ............. | A61C 8/005 433/173 |
| 5,087,200 A * | 2/1992 | Brajnovic | ............. | A61C 8/0068 433/173 |
| 5,125,839 A * | 6/1992 | Ingber | ............. | A61C 8/0001 433/169 |
| 5,620,323 A * | 4/1997 | Bressman | ............. | A61C 8/0022 433/174 |
| 5,662,474 A * | 9/1997 | Jorneus | ............. | A61C 8/005 433/172 |
| 5,667,384 A * | 9/1997 | Sutter | ............. | A61C 8/0048 433/172 |
| 5,863,200 A * | 1/1999 | Hamada | ............. | A61C 8/0048 433/173 |
| 6,048,203 A * | 4/2000 | Rosenberg | ............. | A61C 8/0048 433/172 |
| 6,663,388 B1 * | 12/2003 | Schar | ............. | A61C 8/005 433/173 |
| 6,848,908 B2 * | 2/2005 | Bjorn | ............. | A61C 8/005 433/172 |
| 7,264,469 B2 * | 9/2007 | Abarno | ............. | A61C 1/084 433/173 |
| 9,259,297 B2 * | 2/2016 | Ilter | ............. | A61C 8/0001 |
| 2015/0010883 A1 * | 1/2015 | Garcia Saban | ............. | A61C 8/005 433/173 |

* cited by examiner

*Primary Examiner* — Ralph Lewis
(74) *Attorney, Agent, or Firm* — Dunlap Bennett & Ludwig PLLC; Brendan E. Squire

(57) ABSTRACT

A system, method and apparatus for dental of an anterior tooth. The system includes an abutment having a generally cylindrical post extending from a base. A bore is defined through an anterior face of the post and extends through the base. A protrusion extends from an aft end of the base and is configured to receive a threaded fastener to secure a crown to the abutment. The abutment is secured to a dental implant via a screw extending through the bore into the implant.

15 Claims, 4 Drawing Sheets

SYSTEM, METHOD AND APPARATUS FOR CEMENTLESS RETENTION OF DENTAL CROWNS TO IMPLANTS

BACKGROUND OF THE INVENTION

The present invention relates to dental implants that are inserted into the alveolar bone and, more particularly, to dental implants for anterior teeth.

Dental implants are typically achieved with the surgical implantation of an implant into the patient's alveolar arch and open to the gum line. The implant performs the role of the root structure of a natural tooth to secure a crown of a natural tooth to the patient's jaw. In current practice, a device called an abutment is secured with a retaining screw to the implant to provide a post structure above the gum line to which the crown is then attached, typically by cementation.

Due to the angle between the alveolus and the alignment of most anterior teeth and some posterior teeth, screw retention of crowns to current abutments would require access through the front of the crown or another location that would not provide proper cosmetic results. Accordingly, due to this misalignment, current crowns are cemented to the abutment. Cementation of a crown to an abutment has certain negative consequences. The cemented crown is not easily removable for any required maintenance. In addition, the implant site often reacts adversely to cement which may lead to the loss of the implant.

The most frequent condition that requires maintenance is the loosening of the screw retaining the abutment to the implant. If the retaining screw loosens, destruction of the crown to gain access to the abutment retaining screw is required. This, in turn, necessitates the fabrication of a new crown.

As can be seen, there is a need for an improved system, method and apparatus for the retention of crowns to dental implants.

SUMMARY OF THE INVENTION

In one aspect of the present invention, a dental abutment is provided for attachment of a tooth crown to a dental implant that is implanted in a patient's alveolar arch. The abutment includes a generally cylindrical post extending upwardly from a base. A bore is defined through an anterior face of the post and extends through the base. The bore is configured to be axially aligned with a longitudinal axis of the implant. The base has a protrusion extending from a posterior end and a threaded aperture that is defined in a top surface of the protrusion. The aperture is oriented at an angle to intersect with a longitudinal axis of the bore.

The abutment may also include an annular rim protruding from a bottom end of the base. The annular rim is configured to be received within a shoulder defined in a top end of the dental implant. The threaded aperture is configured to receive a screw to removably secure the crown to the abutment. The angle is between about 10 degrees to about 30 degrees.

Other aspects of the invention include a dental crown for attachment to a dental implant secured in a patient's alveolar arch. The dental crown includes an abutment having a generally cylindrical post extending upwardly from a base. A bore is defined through an anterior face of the post and extends through the base. The base has a protrusion extending from a posterior end and a threaded aperture defined in a top surface of the protrusion, wherein the threaded aperture is angled to intersect with a longitudinal axis of the bore. A crown has a mount with a bulbous body and an interior cavity defined within the mount configured to conform to an outer surface of the abutment. An orifice extends through a posterior end of the mount and is configured to be coaxially aligned with the threaded aperture when the crown is operatively attached to the abutment. A crown may then be applied to a forward surface of the mount.

The dental crown may also include a annular rim protruding from a bottom end of the base, such that the annular rim is configured to be received within a shoulder defined in a top end of the implant. The aperture is configured to receive a screw that removably secures the dental crown to the abutment. The dental crown may also include the dental implant.

Yet other aspects of the invention include a method of dental for replacing a tooth. The method includes forming an abutment having a generally cylindrical post extending upwardly from a base, a bore defined through an anterior face of the post and extending through the base, wherein the bore is configured to be axially aligned with a longitudinal axis of the bore, the base having a protrusion extending from a posterior end and a threaded aperture defined in a top surface of the protrusion, the aperture is oriented at an angle to intersect with a longitudinal axis of the bore.

The method also includes forming a crown of a tooth. The crown is formed to have a mount with a bulbous body, an interior cavity defined within the mount configured to conform to an outer surface of the abutment, an orifice extending through a posterior end of the mount, the orifice configured to be coaxially aligned with the threaded aperture when the crown is operatively attached to the abutment.

Other steps of the method include securing the abutment to a socket implanted in a patient's alveolar arch by applying a threaded fastener through the bore for engagement with a threaded opening in the socket. When the abutment is secured the crown is applied to the abutment. The crown may then be removably secured to the abutment by a threaded fastener received in the orifice and threadingly engaged with the threaded aperture of the socket. The contemplated methods, may also include implanting a socket in a patient's alveolar arch.

These and other features, aspects and advantages of the present invention will become better understood with reference to the following drawings, description and claims.

DETAILED DESCRIPTION OF THE INVENTION

Figure 1:
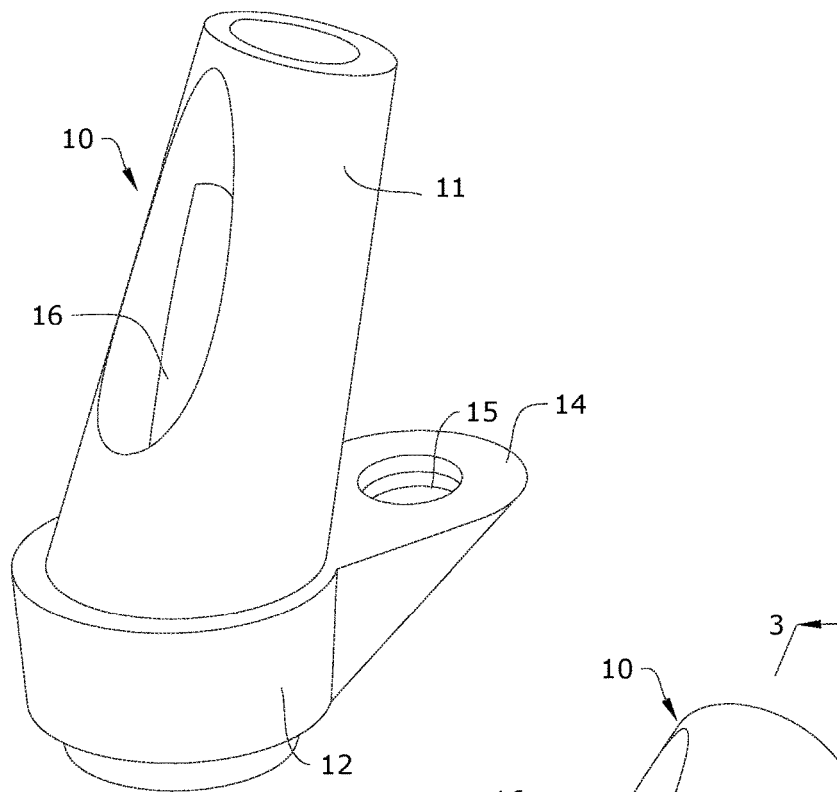
FIG. 1 is a perspective view of an abutment according to aspects of the invention.
Figure 2:
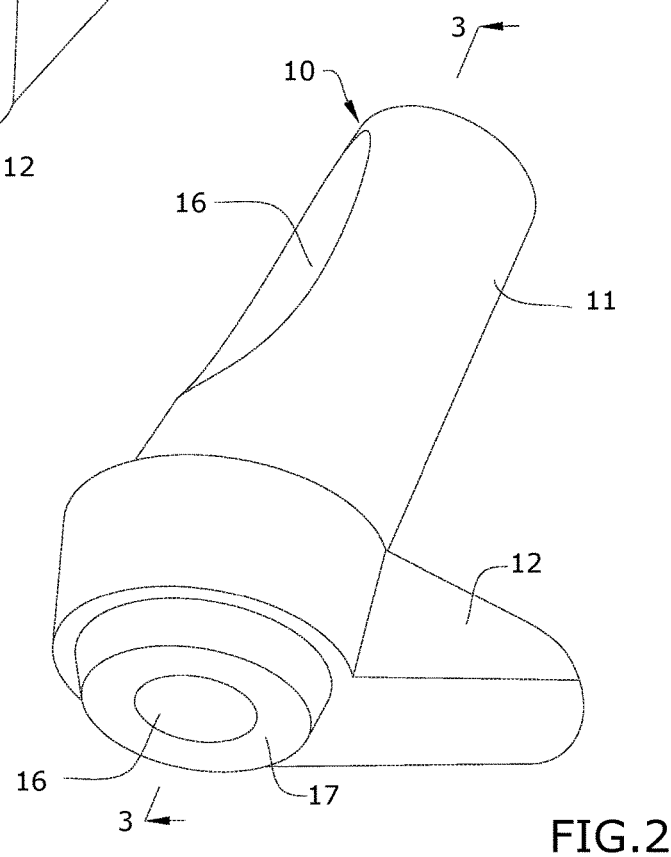
FIG. 2 is a bottom perspective view of the abutment.
Figure 3:
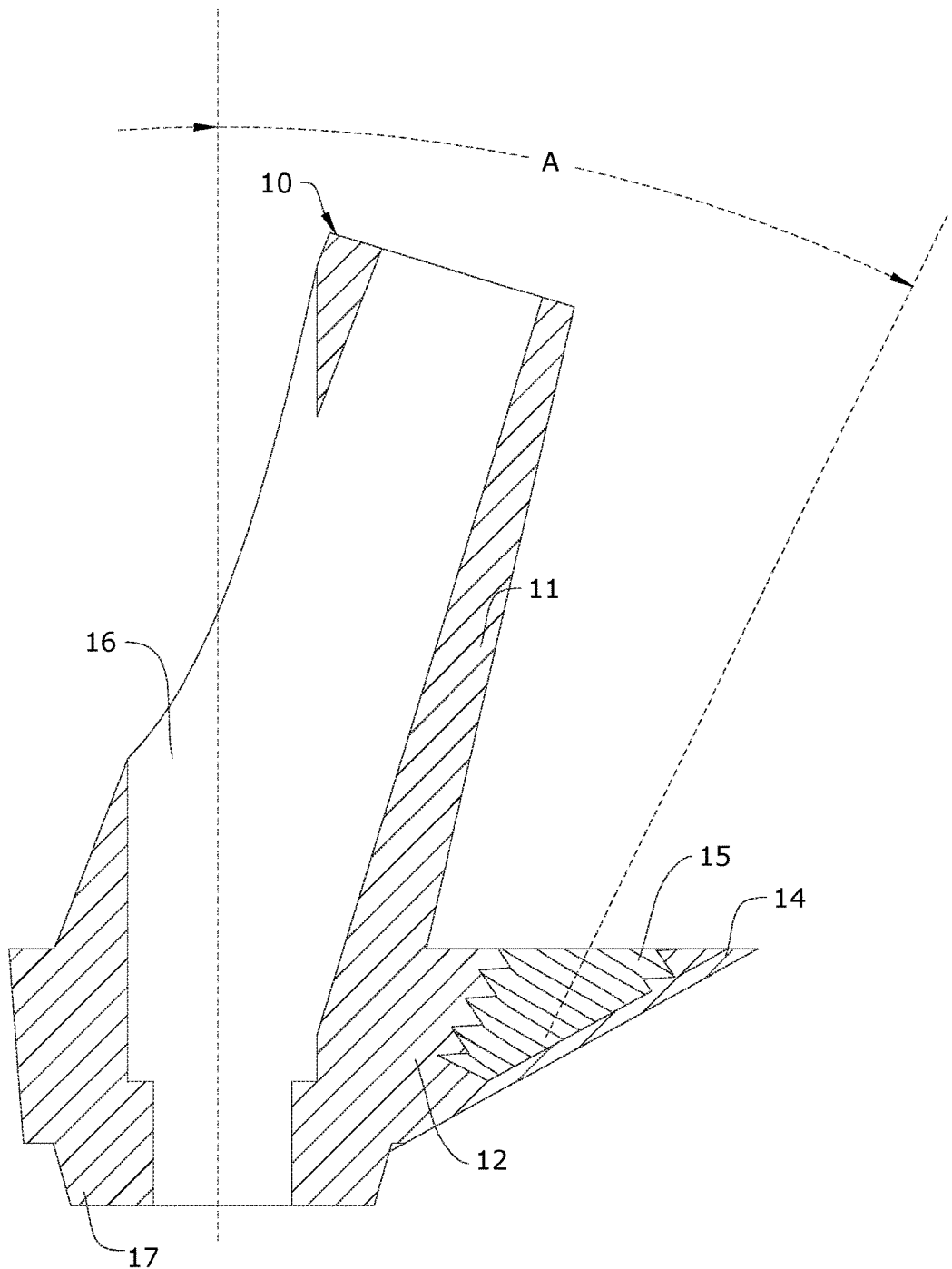
FIG. 3 is a side section view of the abutment taken along line 3-3 of FIG. 2.
Figure 4:
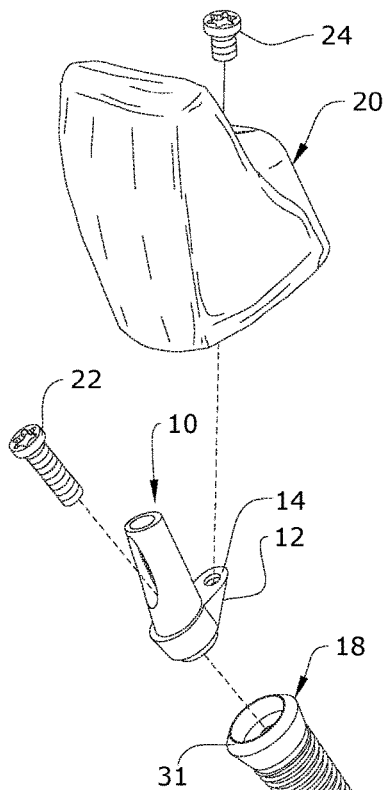
FIG. 4 is an exploded view of a crown and implant structure according to aspects of the invention.
Figure 5:
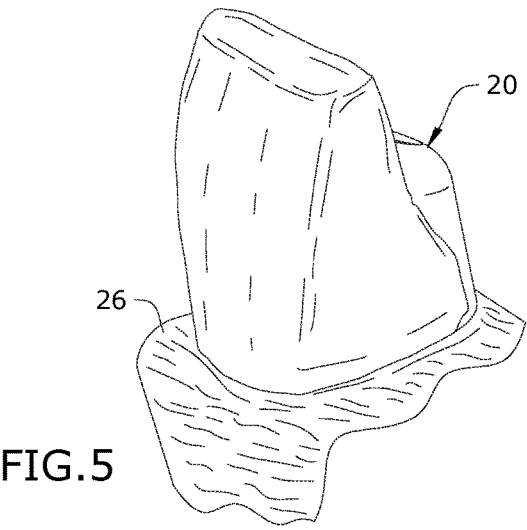
FIG. 5 is a front perspective view of the abutment shown in use securing an tooth crown in a alveolar arch.
Figure 6:
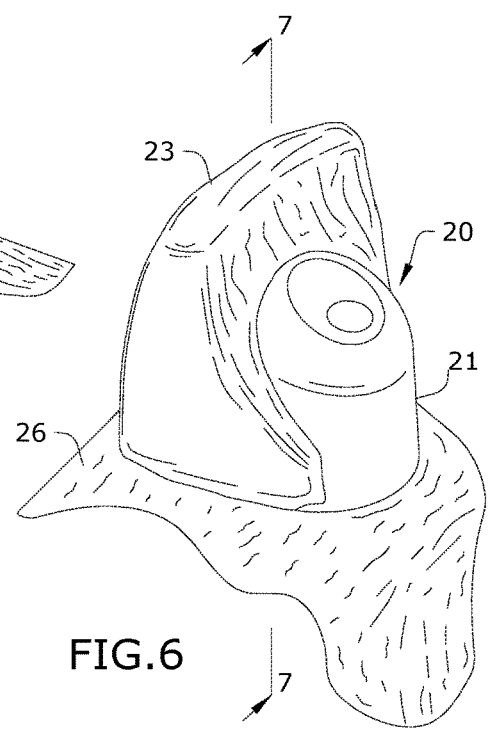
FIG. 6 is a rear perspective view of the abutment shown in use securing an tooth crown in a alveolar arch.
Figure 7:
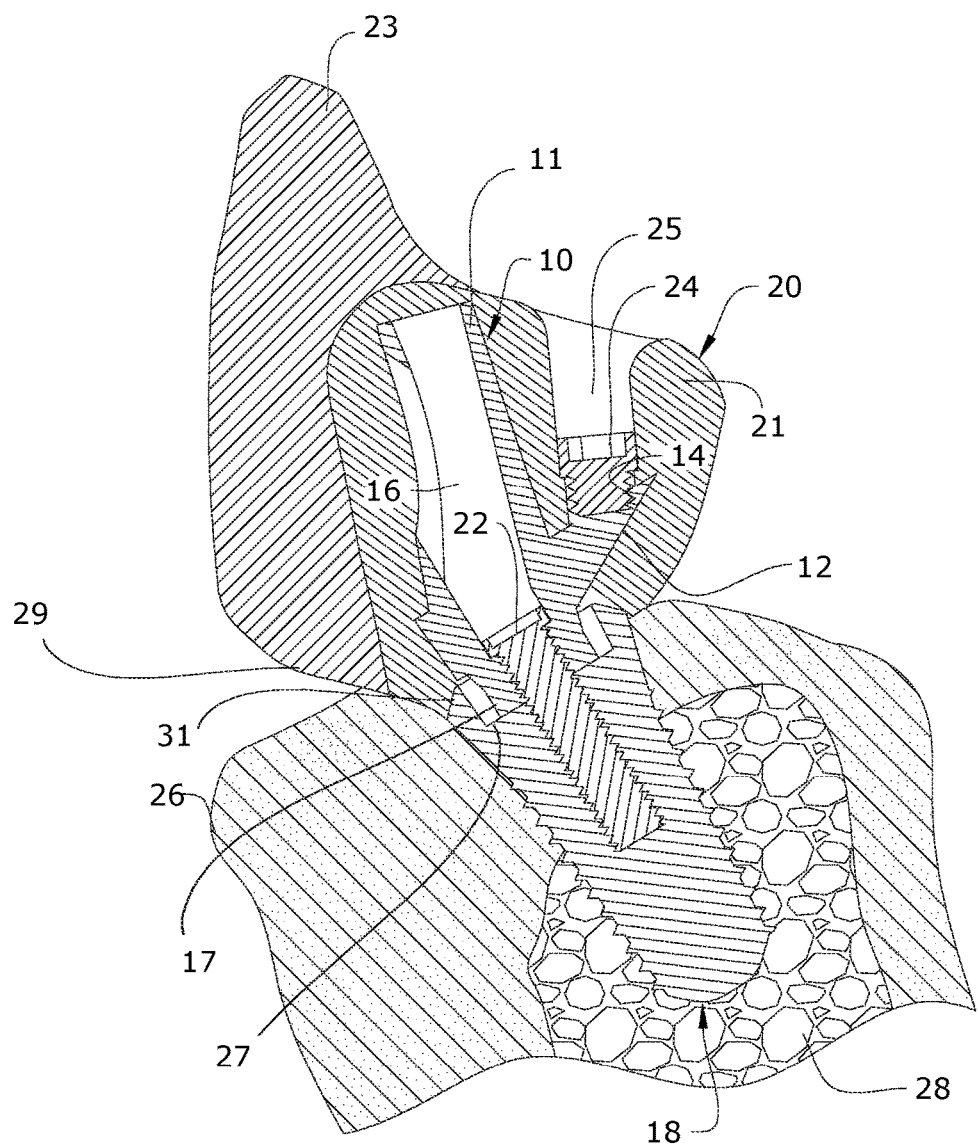
FIG. 7 is a side sectional view of an implant of a crown taken alone line 7-7 in FIG. 6.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides system, method and apparatus for the surgical implantation of a crown 20 for an tooth into a patient's alveolar arch 28.

An abutment 10 according to aspects of the invention, includes a generally cylindrical post 11 extending upwardly from a base 12. The post 11 includes a bore 16 that is defined through an anterior portion of the post 11 and extends through the base 12. The bore 16 is defined at an angle that is anteriorly offset from a vertical axis of the post 11. The bore 16 is axially aligned with a longitudinal axis of an implant 18.

The implant 18 has a lower end that is surgically implanted in the patient's alveolar arch 28 and an upper opening that opens to the patient's gum line 26 when implanted in the patient's alveolar arch 28. The longitudinal axis of the implant 18 is angled anteriorly with the alignment of the alveolar arch 38 so that the implant 18 may have a suitable purchase in the alveolar arch 38. The implant 18 has a threaded bore 19 opening to a top end of the implant 18. The bore 16 receives a threaded fastener 22 that is utilized to secure the abutment 10 to the implant 18.

The base 12 includes a protrusion 14 that extends from a posterior end of the base 12. An aperture 15 is defined in a top surface of the protrusion 14. The aperture 15 is oriented at an angle A with respect to the bore 16 and longitudinal axis of the implant 18 to intersect the longitudinal axis of the implant 18. A bottom end of the base 12 may include an annular rim 17 that is received within a shoulder 27 defined in the opening at the top end of the implant 18. The aperture is configured to receive a screw 24 that removably secures the crown 20 to the abutment 10.

The crown 20 includes a mount 21 portion and a tooth reconstruction 23 portion. The tooth reconstruction 23 is defined with a chamfered lower edge surface 29. Similarly, an anterior portion of the mount 21 has a chamfered bottom edge surface 31. The chamfered lower edge surface 29 and the chamfered bottom edge surface 31 meet at a point below the patient's gum line 26 so that the crown 20 appears to descend into the patients gums 26 as would a natural tooth.

The mount 21 has an orifice 25 that is substantially aligned with a longitudinal axis of the tooth reconstruction 23. The orifice 25 is offset from the longitudinal axis of the implant 18 by an angular offset A corresponding to the difference between the orientation of the implant 18 and the natural alignment of the patient's teeth. The alignment of the orifice 25 with the longitudinal axis of the tooth reconstruction 23 provides a stronger retention of the crown 20. The mount portion 21 includes an interior cavity that is shaped to conform to the outer dimensions abutment 10. The conformity of the mount portion 21 with the abutment 10 improves the strength of the crown 20.

A method of employing the abutment 10 of the present invention includes insertion of the implant 18 according to standard implant techniques. The longitudinal axis of the implant 18 may be advantageously aligned with a vertical thickness of the alveolar arch 28 so that the implant obtains a stronger purchase in the alveolar arch 28.

The dentist may then attach the abutment 10 to the implant 18 by inserting the threaded fastener 22 through the bore 16. The threaded fastener is then tightened to secure the abutment 10 to the implant 18.

The crown 20 may then be fitted to the abutment 10 so that the orifice 25 is aligned with the aperture 15. The threaded fastener 24 may then be inserted through the orifice 25 and tightened to secure the crown to the abutment 10.

It should be understood, of course, that the foregoing relates to exemplary embodiments of the invention and that modifications may be made without departing from the spirit and scope of the invention as set forth in the following claims.

What is claimed is:

1. A dental abutment for attachment of a crown to a dental implant implanted in a patient's alveolar arch, comprising:
    a generally cylindrical post extending upwardly from a base;
    a bore defined through an anterior face of the post and extending through the base, wherein the bore is configured to be axially aligned with a longitudinal axis of the implant;
    the base having a protrusion extending from a posterior end and a threaded aperture defined in a top surface of the protrusion, wherein the aperture is oriented at an angle to intersect with a longitudinal axis of the bore.

2. The dental abutment of claim 1, further comprising:
    an annular rim protruding from a bottom end of the base, wherein the annular rim is configured to be received within a shoulder defined in a top end of the dental implant.

3. The dental abutment of claim 2, wherein the threaded aperture is configured to receive a screw to removably secure the crown to the abutment.

4. The dental abutment of claim 1, wherein the angle is between about 10 degrees to about 30 degrees.

5. A dental crown for attachment to a dental implant implanted in a patient's alveolar arch, comprising:
    an abutment having a generally cylindrical post extending upwardly from a base; a bore defined through an anterior face of the post and extending through the base, the base having a protrusion extending from a posterior end and a threaded aperture defined in a top surface of the protrusion, wherein the threaded aperture is angled to intersect with a longitudinal axis of the bore; and
    a crown having a mount with a bulbous body, an interior cavity defined within the mount configured to conform to an outer surface of the abutment, an orifice extending through a posterior end of the mount, the orifice configured to be coaxially aligned with the threaded aperture when the crown is operatively attached to the abutment.

6. The dental crown of claim 5, further comprising:
    a tooth reconstruction attached to a forward surface of the mount.

7. The dental crown of claim 5, further comprising:
    an annular rim protruding from a bottom end of the base, wherein the annular rim is configured to be received within a shoulder defined in a top end of the implant.

8. The dental crown of claim 5, wherein the aperture is configured to receive a screw that removably secures the dental crown to the abutment.

9. The dental crown of claim 8, further comprising:
    the dental implant.

10. A method of dental reconstruction for replacing a tooth, comprising:
    forming an abutment having a generally cylindrical post extending upwardly from a base, a bore defined through an anterior face of the post and extending through the base, wherein the bore is configured to be axially aligned with a longitudinal axis of an implant configured to be received in a patient's alveolar arch, the base having a protrusion extending from a posterior end and a threaded aperture defined in a top surface of the protrusion, wherein the aperture is oriented at an angle to intersect with a longitudinal axis of the bore.

11. The method of claim 10, further comprising:
forming a crown reconstruction of a tooth having a mount with a bulbous body, an interior cavity defined within the mount configured to conform to an outer surface of the abutment, an orifice extending through a posterior end of the mount, the orifice configured to be coaxially aligned with the threaded aperture when the crown is operatively attached to the abutment.

12. The method of claim 10, further comprising:
securing the abutment to an implant in a patient's alveolar arch by applying a threaded fastener through the bore for engagement with a threaded opening in the socket.

13. The method of claim 12, further comprising:
applying the crown to the abutment.

14. The method of claim 13, further comprising:
securing the crown to the abutment by a threaded fastener received in the orifice and threadingly engaged with the threaded aperture.

15. The method of claim 10, further comprising:
surgically implanting an implant in a patient's alveolar arch.

* * * * *